US00PP10472P

United States Patent [19]

Lemon

[11] Patent Number: Plant 10,472

[45] Date of Patent: Jun. 30, 1998

[54] VARIETY OF GERANIUM PLANT NAMED 'RASPBERRY ICE'

[75] Inventor: David Lemon, Lompoc, Calif.

[73] Assignee: John Bodger & Sons Company, So. El Monte, Calif.

[21] Appl. No.: 724,703

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 9,287 9/1995 Hofmann ..... Plt./87.12

*Primary Examiner*—Howard J. Locker

*Attorney, Agent, or Firm*—Fulwider Patton Lee Utecht, LLP

[57] ABSTRACT

The cultivar is characterized by the light pink bloom with dark pink eye over very dark green foliage. Its quick rooting time and continuous flowering provides for superb cuttings and for quick recovery of the bloom following wet weather conditions. The blooms are very heat tolerant, and an abundant amount of cuttings may be obtained from a single plant.

2 Drawing Sheets

BACKGROUND OF THE NEW PLANT

The present invention comprises a new and distinct cultivar of *Pelargonium×hortorum* known by the varietal name Raspberry Ice (Oglevee No. 2054, Bodger No. 2GM 104-3). The new variety was discovered in a selective breeding program by David Lemon at Bodger Seeds, Ltd., Lompoc, Calif. The new variety is a selection from the crossing of Aphrodite (Bodger No. 10GM 177 unpatented) which has a white flower and medium green leaves with Rio (Bodger No. 10GM 69 unpatented) which has a pink-red bi-colored, single flower as distinguished from the claimed cultivar which has white-pink and Raspberry bi-colored flowers and dark green foliage.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWINGS

The accompanying drawings illustrate the new cultivar, the colors depicted being as nearly true as possible with color illustrations of this type.

Sheet 1 represents a side view of the new cultivar.

Sheet 2 is a top view.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 1, 1996 and flowering on approximately Mar. 14, 1996 under full light and greenhouse, and colorings were taken indoors under 200–220 foot candles of fluorescent cool white light using the R.H.S. Colour Chart of The Royal Horticultural Society of London.

The Plant

Classification:

*Botanical.*—*Pelagronium×hortorum.*

*Commercial.*—Florist's zonal geranium Raspberry Ice (Florist's geraniums are a high quality plant which also grows well outdoors).

Form: Uniform, medium mound habit.

*Height.*—14.5–17.0 cm from top of pot.

*Growth.*—Free basal branching.

*Strength.*—Very heat tolerant; needs no artificial support; free and early flowering.

Foliage: Stalked leaf attachment; very dark green foliage; no zone, present.

Leaves:

*Size.*—8.0–8.5 cm across.

*Shape.*—Reniform with cordate base.

*Margin.*—Crenate.

*Texture.*—Leathery; slightly pubescent.

*Color.*—Top: Green Group 137 A. Bottom: Green Group 137 C. Zone: Not present.

*Ribs and veins.*—Palmate venation: Color: Yellow Green Group 146C.

Petioles:

*Length.*—6.5–7.5 cm.

*Color.*—Yellow-Green Group 146 B.

Stem:

*Color.*—Yellow Green Group 146C.

*Internodes.*—3.0–3.5 cm.

The Bud (Umbel)

Shape: Upright; hemispherical cluster.

Size: 3.0–3.5 cm; bud just showing color.

Inflorescence

Blooming habit: Semi-double; continuous, free and early flowering.

Borne: Umbel; florets on pedicel, pedicel on peduncle; 7.0–10.0 cm above foliage.

Closed florets:

*Bud size.*—1.0 cm in length; 0.5 cm width.

Size:

*Fully open bloom.*—10.0–11.5 cm across.

Open florets:

*Form.*—Flat to slightly cupped; about 21 florets per inflorescence appearing.

*Color.*—Top: Red-Purple Group 65D. Bottom: Red Group 56D. Eye: Red-Purple Group 58C, the appearance of the eye is rather large and on all petals; upper two have veining of Red-Purple Group 61C.

*Petals.*—6–8 in number.

*Size.*—5.0–6.1 cm across.

*Texture and appearance.*—Smooth, satiny; appearance from a distance is a delicate light pink with a prominent eye above dark green foliage.

Petaloids:

*Quantity.*—0–2.

*Shape.*—Elongated, twisted.

*Color.*—Top: Red-Purple Group 65D. Bottom: Red-Purple Group 56D.

Pedicel:

*Length.*—1.6–2.5 cm.

*Color.*—At the base Yellow-Green Group 146 C shading to Greyed-Purple Group 183C at Floret end.

Peduncle:

*Length.*—19.0–20.5 cm.

*Color.*—Yellow-Green Group 146B.

Persistence:

*Disease resistance.*—Not known.

*Lasting quality.*—Raspberry Ice has exceptional heat tolerance and garden performance.

Reproductive Organs

Stamens:

*Athers.*—Length: 2 mm.

*Filaments.*—Length: 7–8 mm. Color: White.

*Pollen.*—Golden Orange.

Pistils:

*Number.*—1.

*Length.*—8.0–9.0 mm.

*Stigma.*—Color: White to very pale pink; 5–6 parted.

*Style.*—Length: 3–4 mm.

Ovaries:

*Color.*—Green, pubescent; superior.

*Length.*—4 mm.

Fruit: None.

General Characteristics

Raspberry Ice is a new and distinct color addition to the Oglevee "Candy" series. The crisp light pink—dark pink eye flower above very dark green foliage is extremely eye catching. This variety has a vigorous plant habit for a dark leaf variety which provides more cuttings. It has performed well in the outdoor trials of 1993, 1994 and the very hot 1995 season.

I claim:

1. A new and distinct variety of geranium plant, substantially as shown and described.

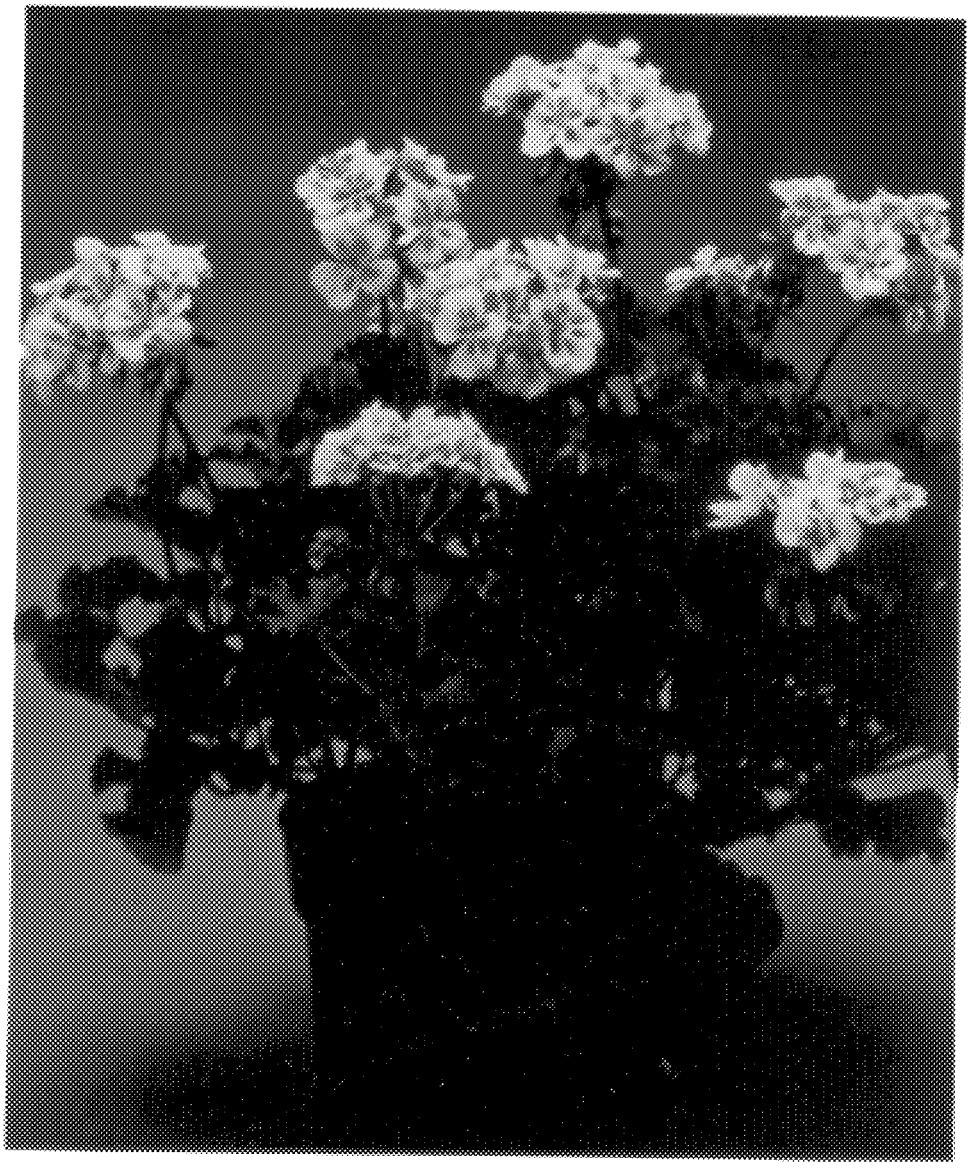

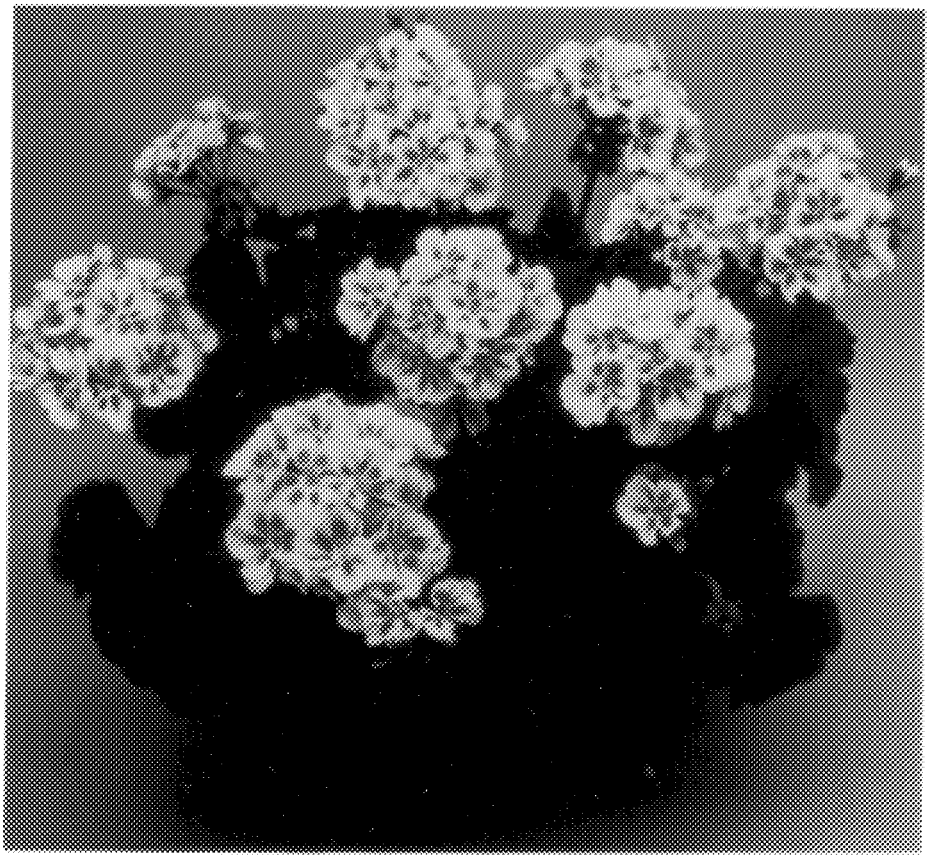

* * * * *